(12) United States Patent
Jain

(10) Patent No.: US 11,167,130 B2
(45) Date of Patent: Nov. 9, 2021

(54) MANIPULATION MEMBER FOR NERVE CUFF

(71) Applicant: MICROTRANSPONDER, INC., Austin, TX (US)

(72) Inventor: Ravi Jain, Austin, TX (US)

(73) Assignee: MICROTRANSPONDER, INC., Austin, TX (US)

( * ) Notice: Subject to any disclaimer, the term of this patent is extended or adjusted under 35 U.S.C. 154(b) by 190 days.

(21) Appl. No.: 16/018,975

(22) Filed: Jun. 26, 2018

(65) Prior Publication Data

US 2019/0388680 A1    Dec. 26, 2019

(51) Int. Cl.
| | | |
|---|---|---|
| *A61N 1/05* | (2006.01) | |
| *A61N 1/36* | (2006.01) | |
| *A61L 31/14* | (2006.01) | |
| *A61B 5/00* | (2006.01) | |

(52) U.S. Cl.
CPC ......... *A61N 1/0556* (2013.01); *A61N 1/3605* (2013.01); *A61B 5/6877* (2013.01); *A61L 31/143* (2013.01); *A61N 1/0558* (2013.01)

(58) Field of Classification Search
CPC .. A61N 1/0556; A61N 1/3605; A61N 1/0558; A61L 31/143; A61B 5/6877
USPC ......................................................... 607/118
See application file for complete search history.

(56) References Cited

U.S. PATENT DOCUMENTS

| | | | |
|---|---|---|---|
| 2014/0378991 A1* | 12/2014 | Ollivier | A61N 1/056 606/129 |
| 2017/0197076 A1* | 7/2017 | Faltys | A61B 5/4839 |
| 2017/0252555 A1* | 9/2017 | Greenberg | A61N 1/375 |

* cited by examiner

*Primary Examiner* — Amanda K Hulbert
*Assistant Examiner* — Philip C Edwards
(74) *Attorney, Agent, or Firm* — Hauptman Ham, LLP

(57) ABSTRACT

A shield member is placed within a polymer flexible carrier in between a manipulation member used to aid implant of a nerve cuff and the nerve to avoid touching the nerve surface with the manipulation member because the texture or material of the flexible member typically causes more foreign body reaction or other biologic reaction from the nerve and surrounding tissues than the polymer of the flexible carrier itself.

38 Claims, 12 Drawing Sheets

MANIPULATION MEMBER FOR NERVE CUFF

CROSS-REFERENCE TO RELATED APPLICATIONS

STATEMENT REGARDING FEDERALLY SPONSORED RESEARCH OR DEVELOPMENT

Not applicable.

REFERENCE TO A MICROFICHE APPENDIX

Not applicable.

BACKGROUND

Nerve cuffs are used to fixate or stabilize a device in a position physically proximate to a nerve. The device typically held by the nerve cuff is an electrical lead from a neurostimulation system or some other medical device. Nerve cuffs may include embedded active devices held in contact with a nerve. Nerve cuffs may be inactive, holding a device that doesn't interact with the nerve, like an insulated portion of a lead, in position alongside the nerve.

Nerve cuffs may be used to fixate a medical device proximate to a nerve so that electrical energy can flow into the nerve sufficient to activate, inhibit or otherwise affect the nerve. Electrically active nerve cuffs may be used to hold leads in place against the nerve so that electrical stimulation may be delivered from a power source to the nerve. Non-electrically active nerve cuffs may be used to hold an insulated portion of a lead in place against a nerve in order to prevent relative motion between the lead and the nerve.

A nerve cuff starts in a closed state, the shape the material will return to and remain in after being deformed into an open state and placed around a nerve. If the nerve is larger in diameter than the closed state of the cuff, the closed state represents the form to which the cuff will attempt to return when placed around the nerve. The polymers used to make the body of the nerve cuffsare formulated to generally resist permanent or lengthy deformation, quickly returning the nerve cuff to the closed state. Metal structures which generally resist permanent or lengthy deformation may also be attached to the polymer as part of the nerve cuff After being flexed or deformed, the cuffs tend to close, returning to their manufactured state.

By manufacturing the nerve cuffs in the closed state, a cuff can be temporarily opened to increase the inner diameter and temporarily increasing the pitch of areas of the cuff, so that the cuff can be placed around a nerve and then released so that the nerve cuff returns to the smaller closed state if the closed state diameter is the same or larger than the nerve diameter, or return to the diameter of the nerve if the closed state diameter is smaller than the nerve diameter, thereby passively fixing the cuff around the nerve.

To aid in opening, placing, manipulating, spinning, translating or rotating a cuff onto or around the nerve, manipulation members may be embedded inside the polymer of the cuff which extend outside of the cuff structure. The user may apply force to these manipulation members using surgical implements or fingers to open and manipulate the cuff rather than trying to manipulate the fragile polymer of the cuff itself.

The nerve itself is very sensitive to foreign bodies, and contact with irritants result in irritation and foreign body responses which may impede desired therapy or be harmful to the patient. The manipulation members, in particular, may have an increased irritation or foreign body response as compared to other materials of the nerve cuff

SUMMARY

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

In an embodiment, the disclosure includes insulating a nerve cuff electrode system that holds an electrode proximate to nerve tissue. The nerve cuff electrode system includes an electrode, a flexible insulating carrier for the electrode, a manipulation member attached to the flexible insulating carrier so that the manipulation member extends beyond an edge of the flexible insulating carrier, and a shield member positioned such that a surface of the shield member is between a portion of the manipulation member and the nerve tissue.

Another embodiment includes a nerve cuff. The nerve cuff includes a flexible insulating carrier whose form includes a void into which a nerve may be placed, a manipulation member connected to the flexible insulating carrier and a shield member positioned such that a surface of the shield member is between a portion of the manipulation member and the void into which a nerve may be placed.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents. The present application describes several embodiments, and none of the statements below should be taken as limiting the claims generally.

Where block diagrams have been used to illustrate the embodiments, it should be recognized that the physical location where described functions are performed are not necessarily represented by the blocks. Part of a function may be performed in one location while another part of the same function is performed at a distinct location. Multiple functions may be performed at the same location. In a functional block diagram, a single line may represent a connection, in general, or a communicable connection, particularly in the presence of a double line, which may represent a power connection. In either case, a connection may be tangible, as in a wire, or radiated, as in near-field communication. An arrow may typically represent the direction of communication or power although should not be taken as limiting the direction of connected flow.

Figure 1:
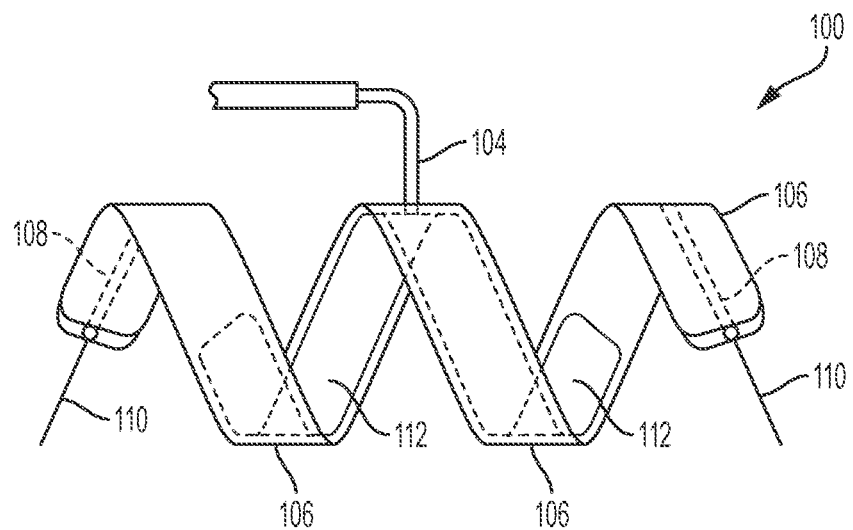
FIG. 1 depicts a helical nerve electrode cuff in accordance with an embodiment.
Figure 2:
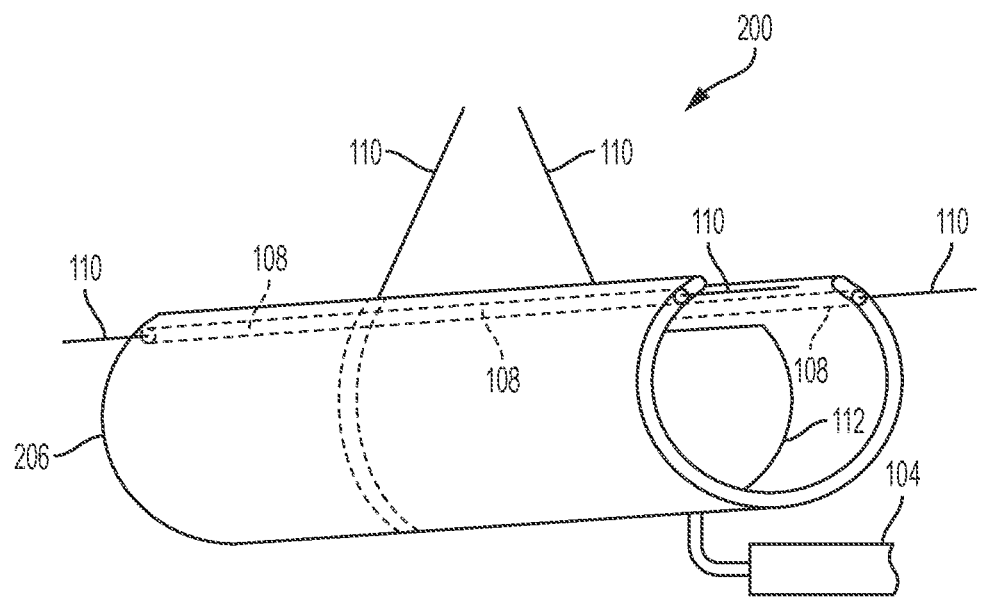
FIG. 2 depicts a cylindrical electrode nerve cuff in accordance with an embodiment.
Figure 3:
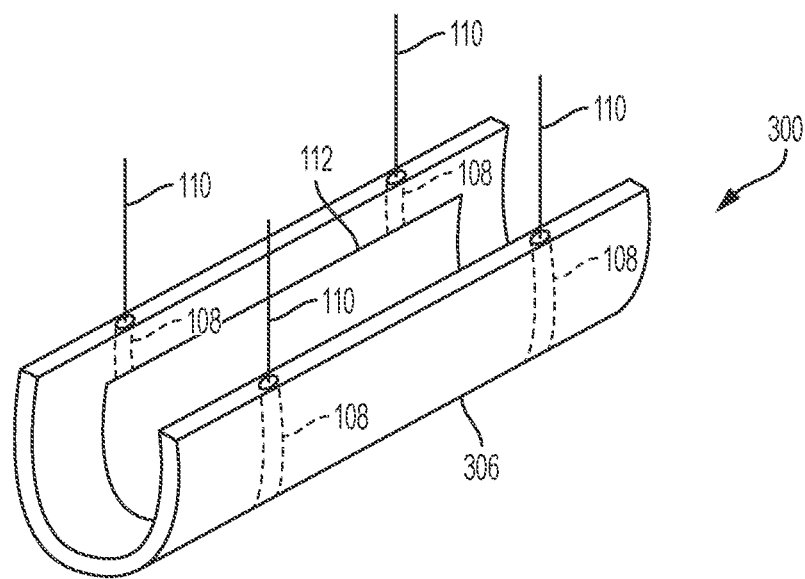
FIG. 3 depicts a cylindrical electrode nerve cuff in accordance with another embodiment.
Figure 4:
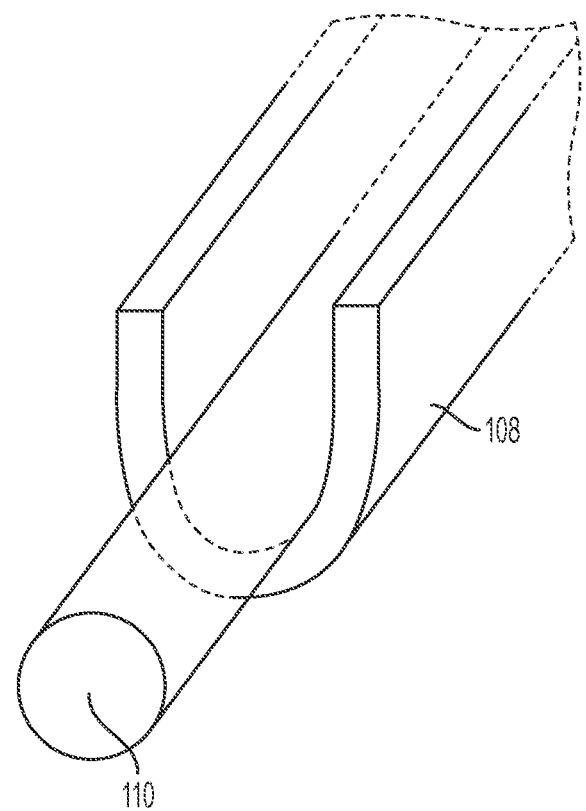
FIG. 4 depicts a shield member configuration in accordance with an embodiment.
Figure 5:
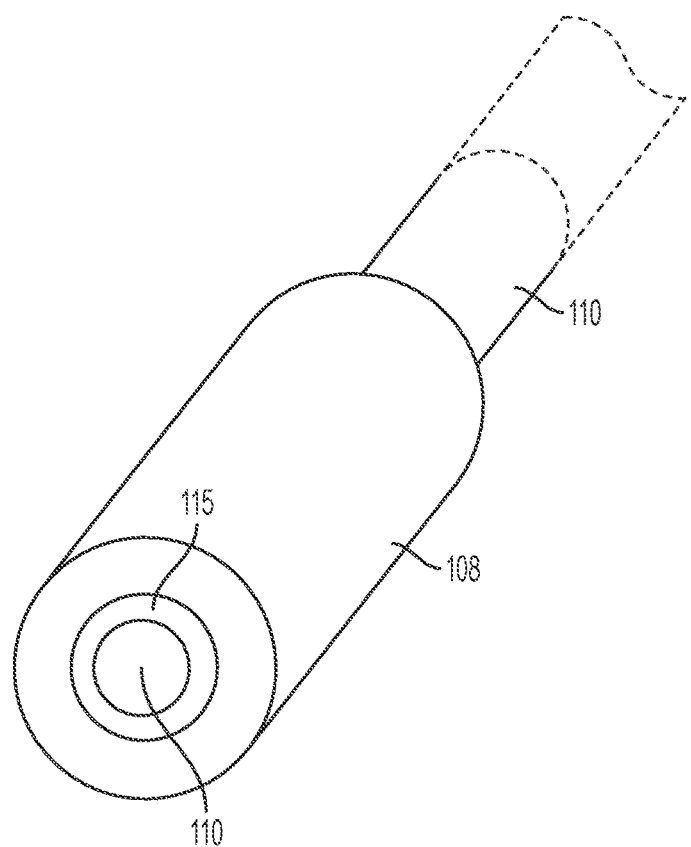
FIG. 5 depicts a shield member configuration in accordance with an embodiment.
Figure 6:
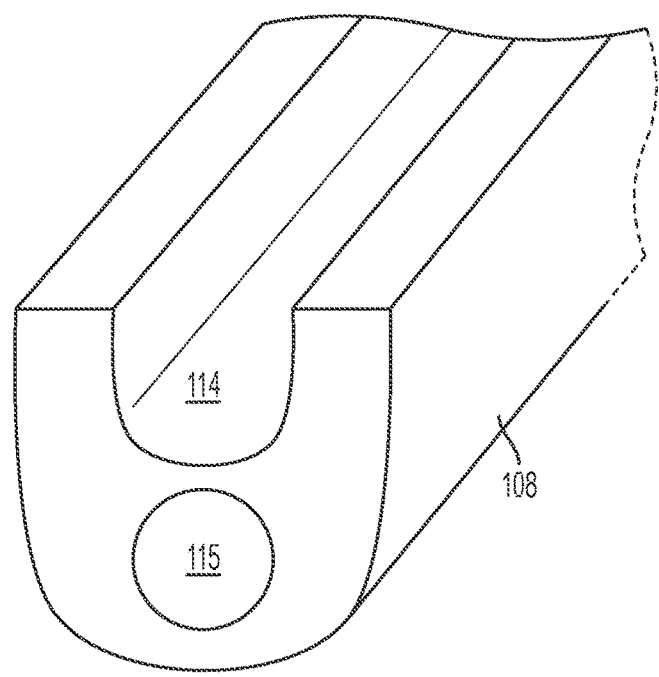
FIG. 6 depicts a shield member configuration in accordance with an embodiment.
Figure 7:
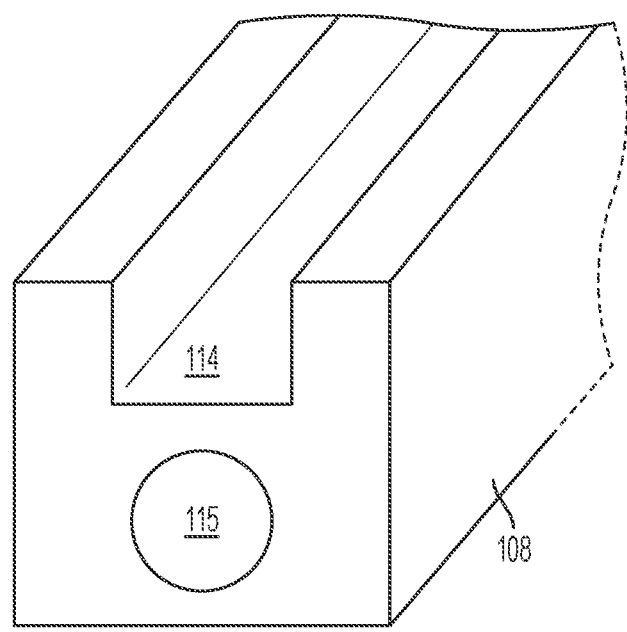
FIG. 7 depicts a shield member configuration in accordance with an embodiment.
Figure 8:
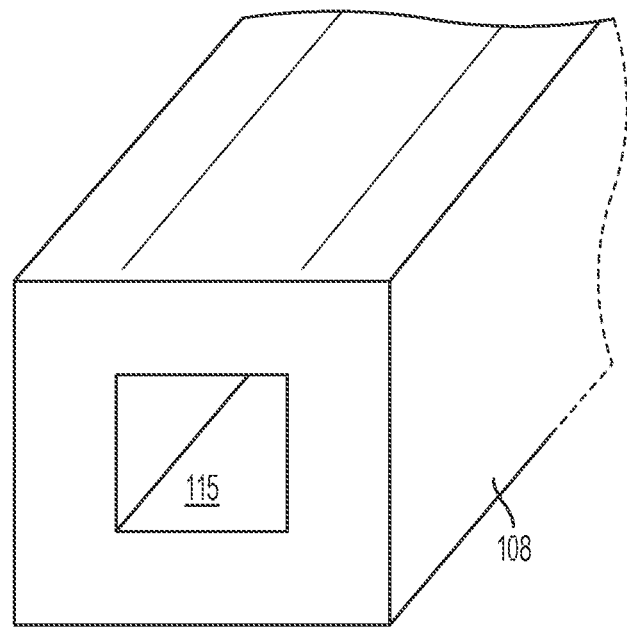
FIG. 8 depicts a shield member configuration in accordance with an embodiment.
Figure 9:
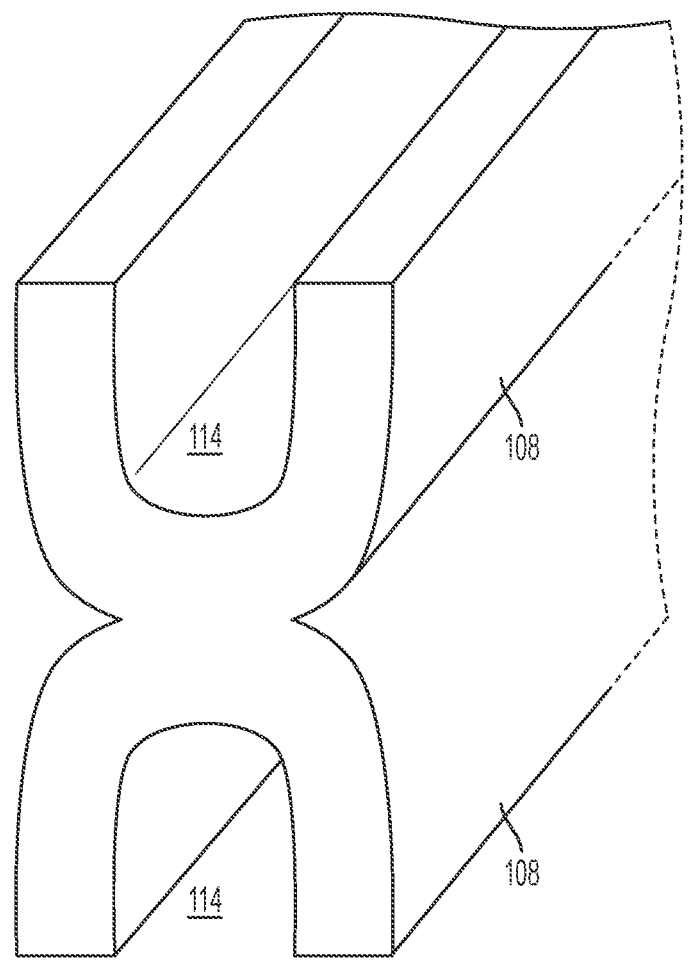
FIG. 9 depicts a shield member configuration in accordance with an embodiment.

With reference to FIG. 1, a spiral or helical electrically active nerve cuff 100 is shown, in accordance with an embodiment. In some embodiments, the nerve cuff 100 wraps around a nerve (not shown). The nerve cuff 100 includes a flexible insulating carrier 106. In some embodiments, the flexible carrier 106 is a helical or spiral shaped piece of polymer. The diameter of the nerve cuff 100 is between 50% and 200% of the diameter of the nerve. The flexible carrier 106 has one or more electrodes 112 exposed on the inner surface of the flexible carrier 106. An elongate conductor 104 connects the electrode 112 to an energy source (not shown) to deliver electrical stimulation to the nerve or to sense electrical activity within the nerve. One or more manipulation members 110 are positioned in or on the flexible carrier 106. In some embodiments, the one or more manipulation members 110 each include one or more flexible tensile load bearing members. The manipulation member 110 is configured to extend beyond an edge of the flexible carrier 106 so they are accessible and capable of being manipulated during placement of the cuff onto the nerve. The manipulation members 110 may be positioned in the flexible carrier 106 within a few millimeters of the nerve-facing surface of the cuff 100. In at least one area of the cuff where each manipulation member 110 is exposed to the flexible carrier 106, encapsulation of the manipulation members 110 by the flexible carrier 106, or material adhesion between the manipulation members 110 and the flexible carrier 106, prevent relative motion between the manipulation members 110 and flexible carrier 106. Force applied to the manipulation members 110 during placement of the cuff onto the nerve are mechanically transmitted to the flexible carrier 106 resulting in a temporary deformation of the flexible carrier 106. The temporary deformation may open the nerve cuff 100. The forces applied to the manipulation members 110 may also result in translation, spinning, and/or rotation of the nerve cuff 100 so that the nerve cuff 100 may be placed to surround or partly surround the nerve. In some embodiments, shield members 108 are placed along some or all of the length of the manipulation members 110 to serve as a barrier between the manipulation members 110 and some or all areas on the nerve where the manipulation members 110 may contact the nerve after placement of the cuff and minimizes foreign body reaction between the manipulation member 110 and the nerve. Encapsulation of shield members 108 by flexible carrier 106, or material adhesion between shield members 108 and flexible carrier 106, may prevent relative motion between shield members 108 and the flexible carrier 106.

In accordance with an embodiment, the electrodes 112 include Platinum, Platinum Iridium alloy or other suitable metals. In some embodiments, the electrodes 112 are configured as ribbons, wires or other suitable configurations.

In accordance with an embodiment, the flexible carrier 106 is a polymer such as silicone, polyurethane, polyester, a mixture of these materials, or any other suitable material.

In accordance with an embodiment, the manipulation members 110 may be polymers or metals or combinations thereof including materials such as polyester, nylon, PTFE, ETFE, stainless steel, nickel-cobalt-chromium-molybdinum alloy, titanium or titanium alloy, nitinol, or other suitable materials. The manipulation members 110 may be solid, hollow, multi-filament, or some combination thereof. The manipulation members may have a cross sectional area of 0.0005 mm$^2$ to 2 mm$^2$.

In accordance with an embodiment, the manipulation members 110 is a single manipulation member 110 exiting the flexible carrier 106 in one or more places. In some embodiments, the manipulation members 110 is multiple single manipulation members 110 exiting the flexible carrier 106 in one or more places.

In accordance with an embodiment, the shield members 108 is a complete or partial barrier between the manipulation members 110 and the inner most diameter of the nerve cuff 100. The shield members 108 are constructed of polymers including silicone, polyurethane, mixtures of these materials, PTFE or ETFE or any other suitable material.

Figure 10:
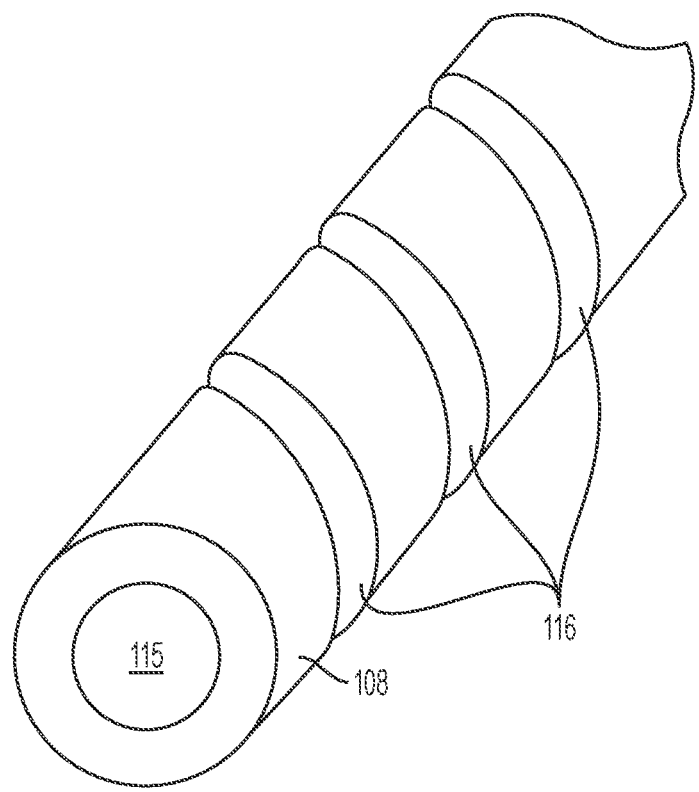
FIG. 10 depicts a shield member configuration in accordance with an embodiment.
Figure 11:
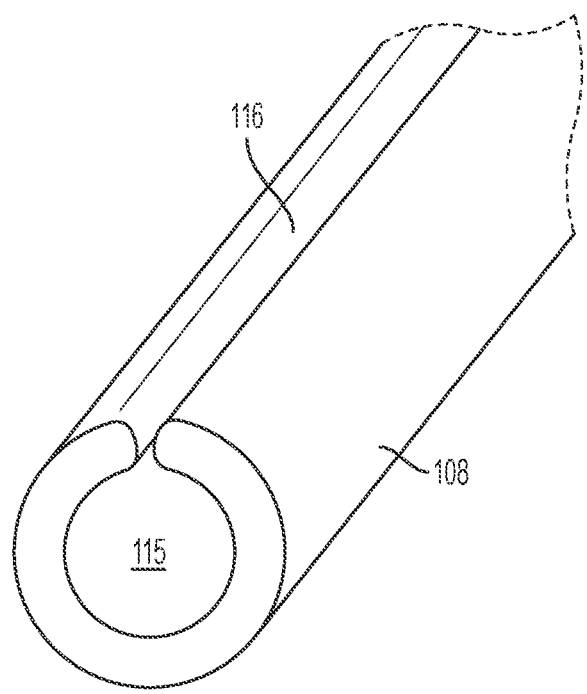
FIG. 11 depicts a shield member configuration in accordance with an embodiment.
Figure 12:
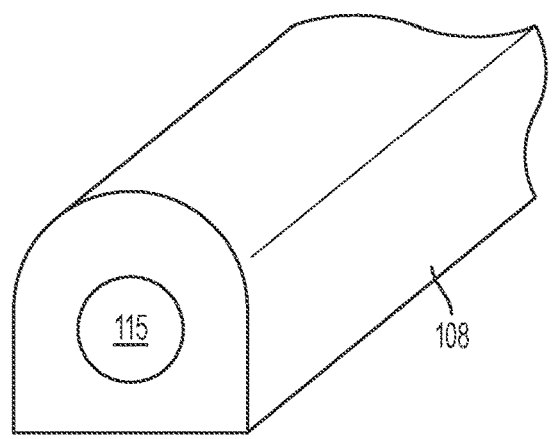
FIG. 12 depicts a shield member configuration in accordance with an embodiment.
Figure 13:
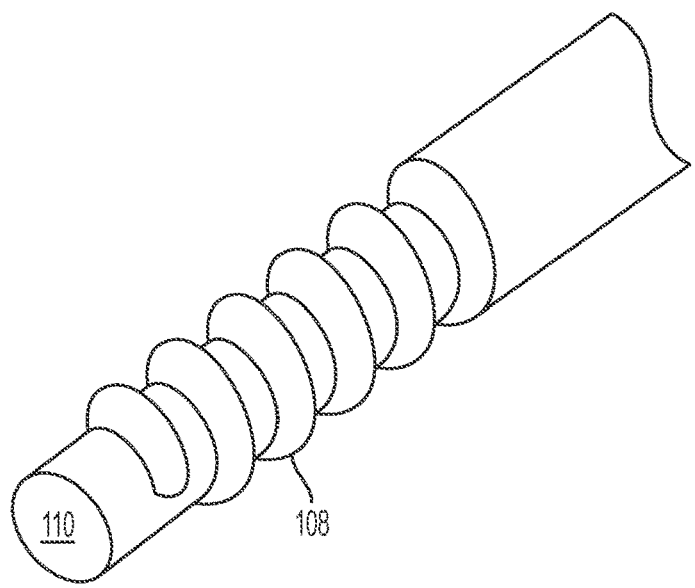
FIG. 13 depicts a shield member configuration in accordance with an embodiment.
Figure 14:
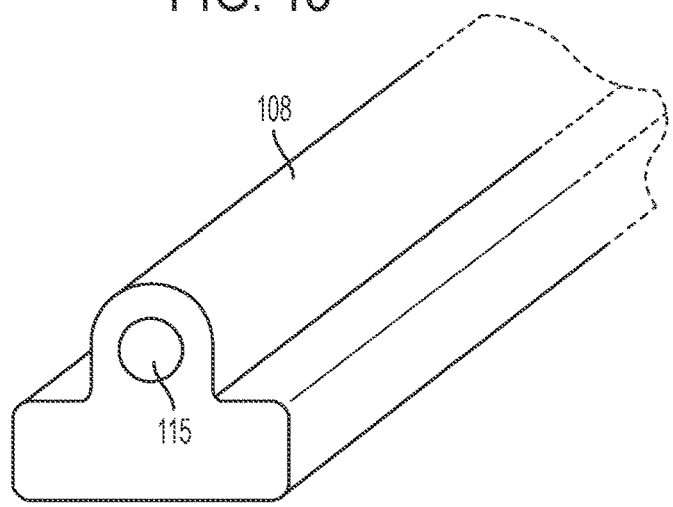
FIG. 14 depicts a shield member configuration in accordance with an embodiment.

FIGS. 5, 6, 7, 8, 10, 11, 12, 14 and 15, in accordance with various embodiments, depict shield members 108 containing a void 115 which allows the shield members 108 to slide over the manipulation members 110. The shield members 108 containing a void 115 may have a slit 116. In some embodiments, the slit 116 is a linear slit as shown in FIG. 11. In some embodiments, the slit 116 is a helical or spiral slit as shown in FIG. 10. In some embodiments, the slit 116 allows for assembly over manipulation members 110 from directions not parallel to the axis of the void 115. In some embodiments, the shield members 108 have a helical or spiral shape as shown in FIG. 13 to allow for assembly over manipulation members 110 from multiple directions.

FIGS. 4, 6, 7, and 9, in accordance with various embodiments, depict the shield members 108 with a groove or recess 114 into which the manipulation member 110 may be positioned or the flexible carrier 106 may be positioned. The grooves or recesses 114 may also increase adhesion between the shield member 108 and flexible carrier 106 and/or shield member 108 and manipulation member 110 because the groove or recess 114 increases the surface area in contact with the flexible carrier 106 and/or manipulation member 110. In some embodiments, the groove or recess 114 may have a smaller cross sectional area than the cross-sectional area of the manipulation member 110 to allow the shield member 108 to deform around the manipulation member 110 after assembly, passively fixating onto the manipulation member 110 within shield member 108.

Figure 16:
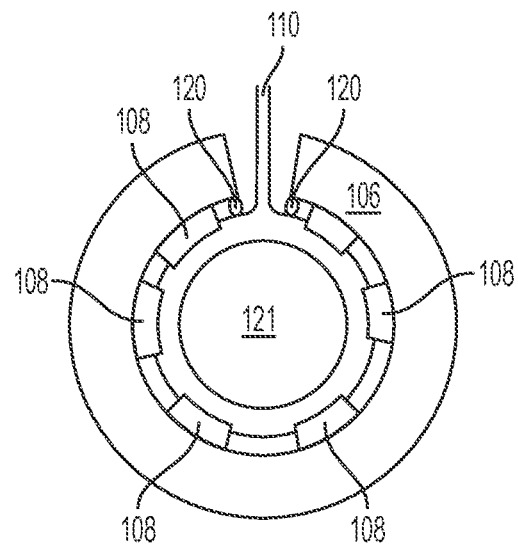
FIG. 16 depicts a nerve cuff configuration in accordance with an embodiment.

FIG. 16, 17, 18, 19, 20, 25 in accordance with various embodiments, non-conductive bonding agents 120 such as epoxy, silicone, cyanoacrylate, or other suitable materials, may be placed between the manipulation members 110 and shield members 108, and/or the manipulation members 110 and flexible carrier 106, and/or the shield members 108 and flexible carrier 106 and prevents relative motion between these elements.

Figure 17:
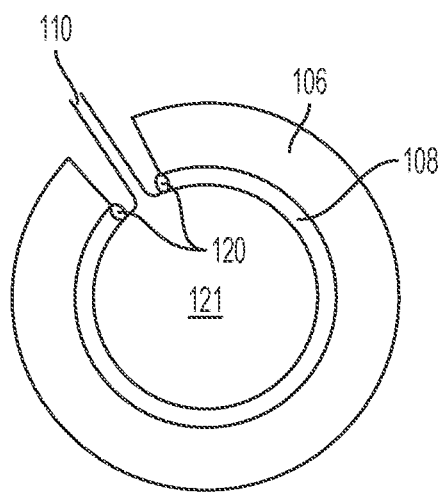
FIG. 17 depicts a nerve cuff configuration in accordance with an embodiment.
Figure 23:
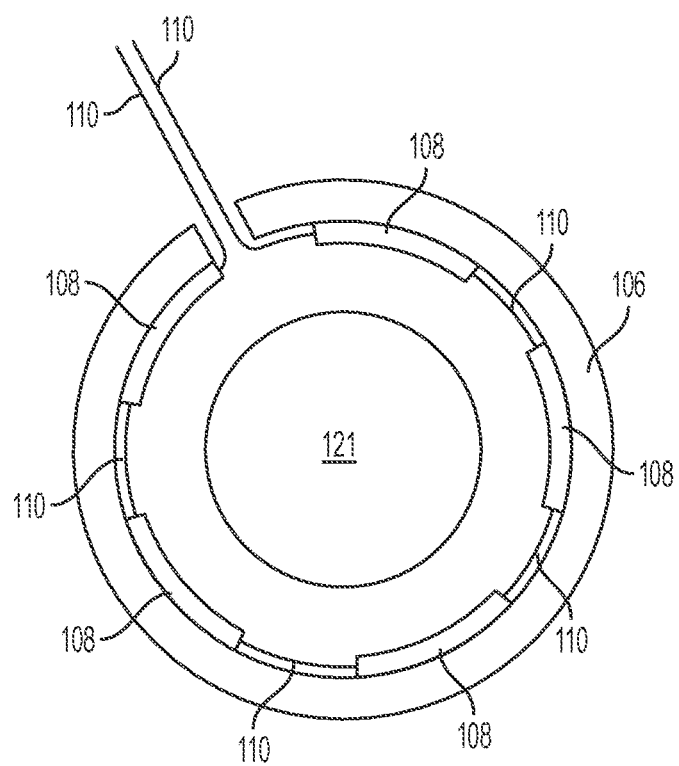
FIG. 23 depicts a nerve cuff configuration in accordance with an embodiment.

The shield members 108 may be a single piece traversing the length of a manipulation member 110 or a portion of a manipulation member 110 within the length of the flexible carrier 106 as depicted in FIG. 17. The shield members 108 may be multiple members spaced between 0.05 mm to 6.35 mm apart along the length of a manipulation member 110 or a portion of a manipulation members 110 within the length of the flexible carrier 106 as depicted in FIG. 23 and FIG. 16. Shield members 108 may be aligned with a surface of the flexible carrier 106 or contained within flexible carrier 106 as depicted in FIG. 23 or extend outside of flexible carrier 106 as depicted in FIG. 16.

Figure 18:
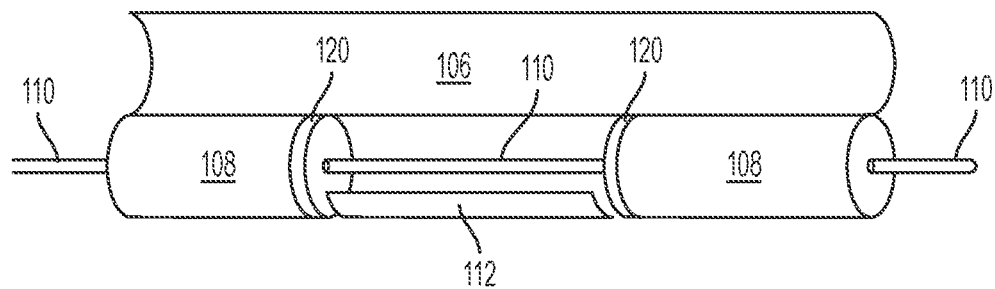
FIG. 18 depicts a nerve cuff configuration in accordance with an embodiment.
Figure 19:
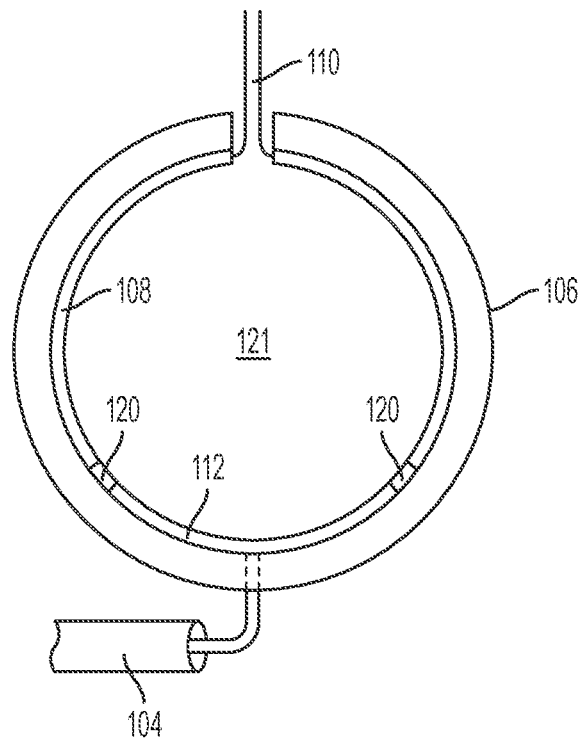
FIG. 19 depicts a nerve cuff configuration in accordance with an embodiment.
Figure 20:
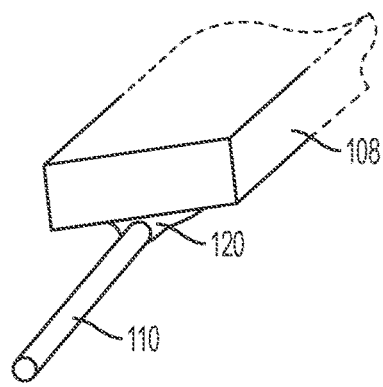
FIG. 20 depicts a shield member configuration in accordance with an embodiment.
Figure 21:
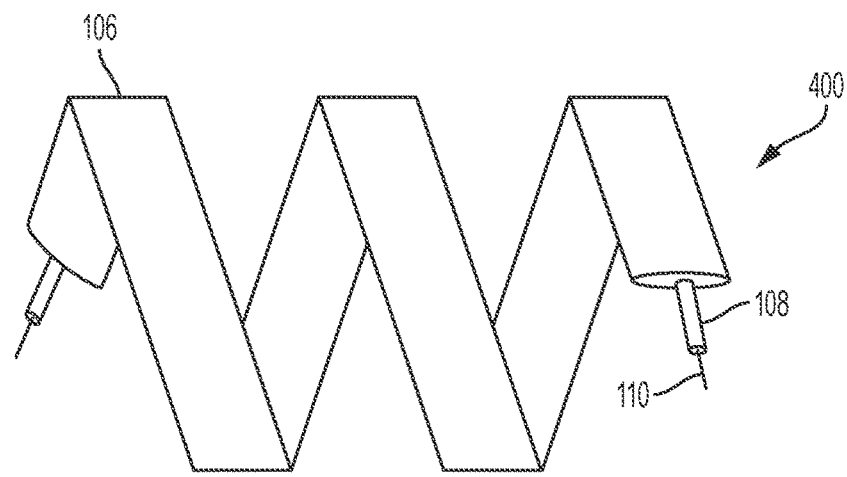
FIG. 21 depicts a helical or spiral nerve cuff in accordance with an embodiment.
Figure 22:
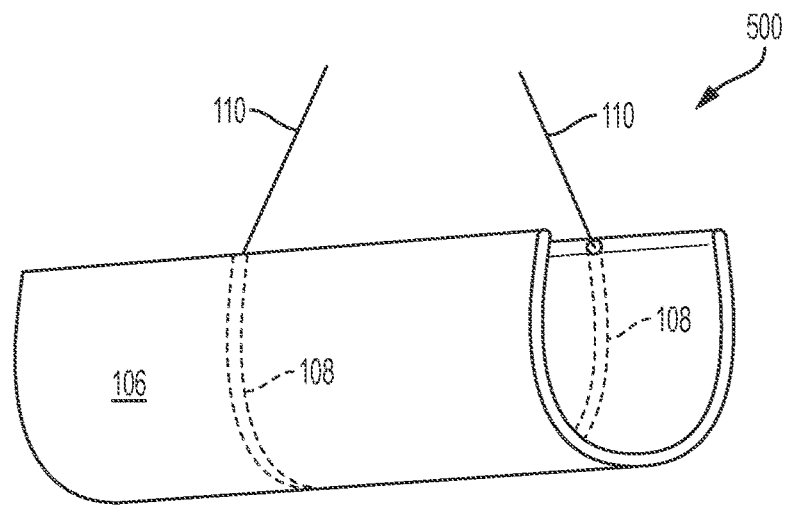
FIG. 22 depicts a cylindrical nerve cuff in accordance with an embodiment.
Figure 24:
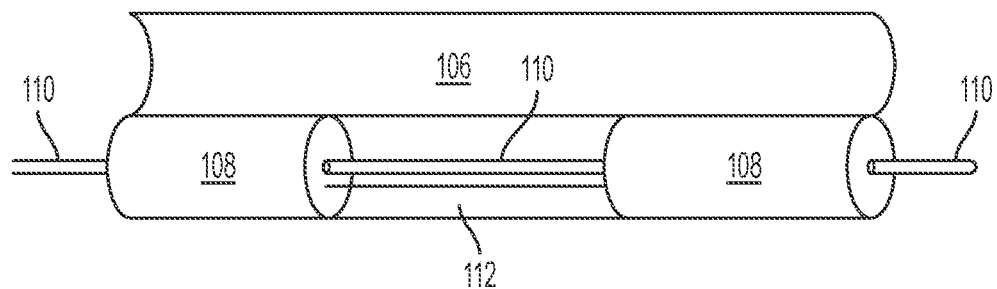
FIG. 24 depicts a nerve cuff configuration in accordance with an embodiment.

FIGS. 18, 19, 24, in accordance with various embodiments, the encapsulating members 108 may abutted to the perimeter of electrode 112 which is exposed to the nerve facing side of the cuff. Bonding agents 120 such as silicone, epoxy, cyanoacrylate, or other suitable materials, material adhesion between shield members 108, electrode 112, and/or flexible carrier 106, and/or encapsulation of the flexible carrier 106 fixate the shield member 108 relative to the exposed electrodes 112 in order to prevent the manipulation member 110 from being exposed on the nerve facing side of the nerve cuff 100 between the shield member 108 and the electrode 112.

FIGS. 16, 17, 19, 23, 25 in accordance with various embodiments, a shield member 108 is positioned such that a surface of shield member 108 is between manipulation member 110 and nerve 121 and avoids direct contact of the nerve surface with the manipulation member 110, as the texture or material of the manipulation member 110 may cause more foreign body or other biologic reaction from the nerve and surrounding tissue than that of the material of the flexible carrier 106 itself or the material of shield member 108 with the nerve or surrounding tissue.

In accordance with various embodiments, manipulation member 110 may be electrically conductive and electrically connected to electrode 112 within the cuff. Shield member 108 may be positioned such that a surface of shield member 108 is between manipulation member 110 and nerve 121 and avoids the manipulation member 110 touching the nerve surface or other bioconductive materials around the nerve and prevents a reduction in the density of current delivered to or sensed from the nerve using electrode 112.

FIGS. 18, 24, in accordance with various embodiments, the manipulation members 110 are placed on the side of the electrodes 112 opposite from the electrode 112 surface facing the nerve and does not reduce the surface area of the electrode 112 interacting with the nerve.

Figure 15:
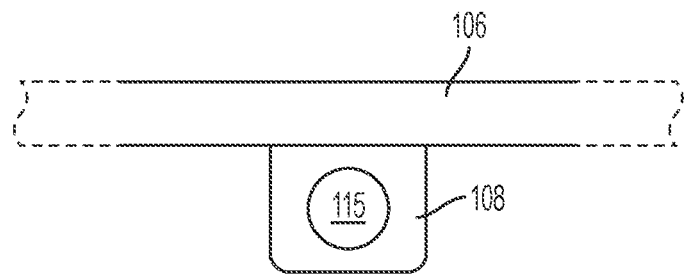
FIG. 15 depicts a shield member configuration in accordance with an embodiment.

FIG. 15, 16, 19, 23, in an embodiment, multiple shield members 108 are individually spaced along the manipulation member 110 and flexible carrier 106 between about 0.05 to 6.35 mm apart. The shield members 108 abut an inner diameter surface of flexible carrier 106. The shield member 108 is positioned such that a surface of shield member 108 is between manipulation member 110 and nerve 121. Bonding agents 120, encapsulation of flexible carrier 106, and/or material adhesion of the flexible carrier 106 prevent relative motion between the manipulation member 110, shield members 108, and flexible carrier 106. In FIG. 16, in an embodiment, the inherent rigidity of the manipulation member 110 results in no portion of the manipulation member 110 not covered or supported by shield members 108 is radially closer to the center of the cuff than the closest radial point of the shield member 108 to the center of the cuff. When the nerve cuff is placed on the nerve, manipulation member 110 is elevated above the nerve surface by shield members 108. In FIG. 23, the flexible carrier 106 is shaped to fill gaps between shield members 108 on the nerve facing side of the cuff and provides a more uniform surface on the nerve facing side of the cuff. In FIG. 19, bonding agents 120 may be used to fill gaps between shield members 108 and/or between shield members 108 and electrodes 112 and provides a more uniform surface on the nerve facing side of the cuff.

Figure 25:
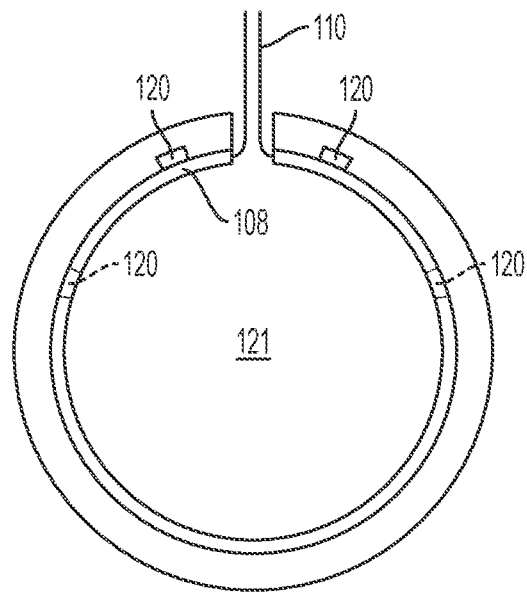
FIG. 25 depicts a nerve cuff configuration in accordance with an embodiment.

FIG. 17 and FIG. 25, in an embodiment, a single shield members 108 is placed along the manipulation member 110 and flexible carrier 106. The shield member 108 abuts an inner diameter surface of flexible carrier 106. The shield member 108 is positioned such that a surface of shield member 108 is between manipulation member 110 and nerve 121 at all points along the length of the manipulation member within the length of the flexible carrier 106. Bonding agents 120, encapsulation of flexible carrier 106, and/or material adhesion of the flexible carrier 106 at least reduce relative motion between the manipulation member 110, shield members 108, and flexible carrier 106.

FIGS. 2, 3, 4, 5, 6, 7, 8, 9, 10, 11, 12, 13, 14, 15, 16, 17, 18, 19, 20, 23, 24, 25 in accordance with various embodiments, depict a cylindrical, electrically active nerve cuff 200 utilizing one or more electrodes 112, elongate conductor 104, flexible carrier 106, shield members 108 and manipulation members 110. The shield members 108 and manipulation members 110 may be oriented parallel to the axis of the cuff 200 or at an angle to the axis of the cuff 200. The diameter of the nerve cuff 200 ranges between 50% and 200% of the diameter of the nerve. The flexible carrier 106 has one or more electrodes 112 exposed on the inner surface of the flexible carrier 106. An elongate conductor 104 connects the electrode 112 to an energy source (not shown)

and delivers electrical stimulation to the nerve or senses electrical activity within the nerve. One or more manipulation members 110 are positioned in or on flexible carrier 106. A manipulation member 110 is configured to extend beyond an edge of the flexible carrier 106 so they are accessible and capable of being manipulated during placement of the cuff onto the nerve. The manipulation members 110 may be positioned in flexible carrier 106 within a few millimeters of the nerve facing surface of the cuff 100. Bonding agents, encapsulation of manipulation members 110 by flexible carrier 106, material adhesion between manipulation members 110 and flexible carrier 106, or material adhesion between the manipulation member 110 and shield member 108 coupled with encapsulation of the shield member by flexible carrier 106 or material adhesion between shield member 108 and flexible carrier 106 at least reduce relative motion between manipulation members 110 and flexible carrier 106. One or more forces applied to the manipulation members 110 during placement of the cuff onto the nerve are mechanically transmitted to the flexible carrier 106 resulting in a temporary deformation of the flexible carrier 106. The temporary deformation may open the nerve cuff 100. The one or more forces applied to the manipulation members 110 may also result in translation, spinning, and/or rotation of the nerve cuff 100 and allows the nerve cuff 100 to surround or partly surround the nerve. Shield members 108 are placed along some or all of the length of the manipulation members 110 to serve as a barrier between the manipulation members 110 and some or all areas on the nerve where the manipulation members 110 may contact the nerve after placement of the cuff in order to minimize foreign body reaction between the manipulation member 110 and the nerve. Encapsulation of shield members 108 by flexible carrier 106, or material adhesion between shield members 108 and flexible carrier 106, may prevent relative motion between shield members 108 and flexible carrier 106.

FIGS. 21, 4, 5, 6, 7, 8, 9, 10, 11, 12, 13, 14, 15,16,17, 20, 23, in accordance with various embodiments, depict a spiral or helical non-electrically active nerve cuff 400 utilizing flexible carrier 106, shield members 108, and manipulation members 110. The diameter of the nerve cuff 400 ranges between 50% and 200% of the diameter of the nerve. One or more manipulation members 110 are positioned in or on flexible carrier 106. A manipulation member 110 is configured to extend beyond an edge of the flexible carrier 106 so they are accessible and capable of being manipulated during placement of the cuff onto the nerve. The manipulation members 110 may be positioned in flexible carrier 106 within a few millimeters of the nerve facing surface of the cuff 400. Bonding agents, encapsulation of manipulation members 110 by flexible carrier 106, material adhesion between manipulation members 110 and flexible carrier 106, or material adhesion between the manipulation member 110 and shield member 108 coupled with encapsulation of the shield member by flexible carrier 106 or material adhesion between shield member 108 and flexible carrier 106 at least relative motion between manipulation members 110 and flexible carrier 106. One or more forces applied to the manipulation members 110 during placement of the cuff onto the nerve are mechanically transmitted to the flexible carrier 106 resulting in a temporary deformation of the flexible carrier 106. The temporary deformation may open the nerve cuff 100. The one or more forces applied to manipulation members 110 may also result in translation, spinning, and/or rotation of the nerve cuff 100 and allows the nerve cuff 100 to surround or partly surround the nerve. Shield members 108 are placed along some or all of the length of the manipulation members 110 to serve as a barrier between the manipulation members 110 and some or all areas on the nerve where the manipulation members 110 may contact the nerve after placement of the cuff in order to minimize foreign body reaction between the manipulation member 110 and the nerve. Encapsulation of shield members 108 by flexible carrier 106, or material adhesion between shield members 108 and flexible carrier 106, may at least reduce relative motion between shield members 108 and flexible carrier 106.

FIGS. 4, 5, 6, 7, 8, 9, 10, 11, 12, 13, 14, 15, 16, 17, 20, 22, 23, in accordance with various embodiments, depict a cylindrical non-electrically active nerve cuff 500 utilizing flexible carrier 106, shield members 108, and manipulation members 110. The diameter of the nerve cuff ranges from 50% and 200% of the diameter of the nerve. One or more manipulation members 110 are positioned in or on flexible carrier 106. A manipulation member 110 is configured to extend beyond an edge of the flexible carrier 106 so they are accessible and capable of being manipulated during placement of the cuff onto the nerve. The manipulation members 110 may be positioned in the flexible carrier 106 within a few millimeters of the nerve facing surface of the cuff 100. Bonding agents, encapsulation of manipulation members 110 by flexible carrier 106, material adhesion between manipulation members 110 and flexible carrier 106, or material adhesion between the manipulation member 110 and shield member 108 coupled with encapsulation of the shield member by flexible carrier 106 or material adhesion between shield member 108 and flexible carrier 106 at least reduce relative motion between manipulation members 110 and flexible carrier 106. One or more forces applied to the manipulation members 110 during placement of the cuff onto the nerve are mechanically transmitted to the flexible carrier 106 resulting in a temporary deformation of the flexible carrier 106. The temporary deformation may open the nerve cuff 100. The one or more forces applied to the manipulation members 110 may also result in translation, spinning, and/or rotation of the nerve cuff 100 and allows the nerve cuff 100 to surround or partly surround the nerve. Shield members 108 are placed along some or all of the length of the manipulation members 110 to serve as a barrier between the manipulation members 110 and some or all areas on the nerve where the manipulation members 110 may contact the nerve after placement of the cuff in order to minimize foreign body reaction between the manipulation member 110 and the nerve. Encapsulation of shield members 108 by flexible carrier 106, or material adhesion between shield members 108 and flexible carrier 106, may at least reduce relative motion between shield members 108 and flexible carrier 106.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 5, 4, etc.; greater than 0.10 includes 0.11, 0.12, 0.15, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 5 percent, 4 percent, 5 percent, . . . , 50 percent, 51 percent, 52 percent, . . . , 75 percent, 76 percent, 77 percent, 78 percent, 77 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A nerve cuff electrode system comprising: an electrode; a flexible carrier for the electrode, the flexible carrier being insulating; a manipulation member attached to the flexible carrier, and extending beyond an edge of the flexible carrier; and a shield member and having a surface between a portion of the manipulation member and nerve tissue, and wherein the shield member is attached to the flexible carrier to prevent relative motion between the shield member and the flexible carrier and wherein the shield member is attached to the manipulation member to prevent relative motion between the shield member and the manipulation member.

2. The nerve cuff electrode system of claim 1, wherein the shield member is placed around an outer surface of the manipulation member.

3. The nerve cuff electrode system of claim 2, wherein the shield member surrounds the outer surface of the manipulation member.

4. The nerve cuff electrode system of claim 1, wherein the shield member is a geometric solid having a hole that extends through the shield member.

5. The nerve cuff electrode system of claim 1, wherein the shield member is a geometric solid having a channel in a surface of the shield member.

6. The nerve cuff electrode system of claim 1 wherein the shield member has a hole that extends through the shield member, the hole containing a portion of the manipulation member.

7. The nerve cuff electrode system of claim 1, wherein the shield member has a channel containing a portion of the manipulation member.

8. The nerve cuff electrode system of claim 1, wherein the shield member has a helical shape.

9. The nerve cuff electrode system of claim 1, wherein the shield member is an insulating material selected from a group consisting of silicone, polyurethane, ETFE, PTFE, and combinations thereof.

10. The nerve cuff electrode system of claim 1, wherein the shield member is a split tube.

11. The nerve cuff electrode system of claim 1, wherein the shield member is bonded to the manipulation member by a bonding material.

12. The nerve cuff electrode system of claim 11, wherein the bonding material is selected from a group consisting of silicone, epoxy, cyanoacrylate, and combinations thereof.

13. The nerve cuff electrode system of claim 1, wherein the shield member is bonded to the flexible carrier by a bonding material.

14. The nerve cuff electrode system of claim 13 wherein the bonding material is selected from a group consisting of silicone, epoxy, cyanoacrylate and combinations thereof.

15. The nerve cuff electrode system of claim 1, wherein the shield member is bonded to the electrode by a bonding material.

16. The nerve cuff electrode system of claim 15, wherein the bonding material is selected from a group consisting of silicone, epoxy, and cyanoacrylate and combinations thereof.

17. The nerve cuff electrode system of claim 1, wherein the shield member is configured to interlock with the flexible insulating carrier.

18. The nerve cuff electrode system of claim 1, wherein the shield member interlocks with the manipulation member.

19. The nerve cuff electrode system of claim 1, wherein the shield member is attached to the flexible carrier to prevent relative motion between the shield member and the flexible carrier in an axial direction with respect to the manipulation member.

20. A nerve cuff comprising: a flexible carrier which is insulating and whose form includes a void into which a nerve may be positioned; a manipulation member connected to the flexible carrier wherein the manipulation member extends beyond an edge of the flexible carrier; and a shield member and positioned such that a surface of the shield member is between a portion of the manipulation member and the void, and wherein the shield member is bonded to the flexible carrier to prevent relative motion between the shield member and the flexible carrier and wherein the shield member is bonded to the manipulation member to prevent relative motion between the shield member and the manipulation member.

21. The nerve cuff of claim 20 wherein the shield member comprises more than one shield member and wherein the shield members are positioned around an outer surface of the manipulation member.

22. The nerve cuff of claim 20 wherein the shield member comprises more than one shield member and wherein the shield members surround an outer surface of the manipulation member.

23. The nerve cuff of claim 20 wherein the shield member is a geometric solid having a through hole formed therein.

24. The nerve cuff of claim 20 wherein the shield member is a geometric solid containing a channel in a surface of the geometric solid.

25. The nerve cuff of claim 20 wherein the shield member has a through hole containing a portion of the manipulation member.

26. The nerve cuff of claim 20 wherein the shield member has a channel containing a portion of the manipulation member.

27. The nerve cuff of claim 20 wherein the shield member is helical shaped.

28. The nerve cuff of claim 20, wherein the shield member is made of one or more of the group consisting of silicone, polyurethane, ETFE, and PTFE.

29. The nerve cuff of claim 20 wherein the shield member is a split tube.

30. The nerve cuff claim 20 wherein the shield member is bonded with a material (bonding material) to the manipulation member.

31. The nerve cuff of claim 30 wherein the bonding material comprises silicone, epoxy, cyanoacrylate, and mixtures thereof.

32. The nerve cuff of claim 20 wherein the shield member is bonded with a material (bonding material) to the flexible carrier.

33. The nerve cuff of claim 32 wherein the bonding material comprises silicone, epoxy, cyanoacrylate, and mixtures thereof.

34. The nerve cuff of claim 20 further comprising an electrode on the nerve cuff; and wherein the shield member is bonded with a material (bonding material) to an electrode.

35. The nerve cuff of claim 34 wherein the bonding material comprises silicone, epoxy, cyanoacrylate, and mixtures thereof.

36. The nerve cuff of claim 20 wherein the shield member interlocks with the flexible insulating carrier.

37. The nerve cuff of claim 20 wherein the shield member interlocks with the manipulation member.

38. The nerve cuff of claim 20, wherein the shield member is bonded to the flexible carrier to prevent relative motion between the shield member and the flexible carrier in an axial direction with respect to the manipulation member.

* * * * *